(12) United States Patent
Boehringer et al.

(10) Patent No.: US 7,887,564 B2
(45) Date of Patent: Feb. 15, 2011

(54) METHOD FOR TREATING A WOUND

(75) Inventors: John R. Boehringer, Wynnewood, PA (US); John Karpowicz, Chester Springs, PA (US); Christopher L. Radl, Malvern, PA (US); Jacob L. Timm, Hancock, NH (US); Amitabha Mitra, Voorhees, NJ (US)

(73) Assignee: Boehringer Technologies, L.P., Phoenixville, PA (US)

( * ) Notice: Subject to any disclaimer, the term of this patent is extended or adjusted under 35 U.S.C. 154(b) by 191 days.

(21) Appl. No.: 12/327,152

(22) Filed: Dec. 3, 2008

(65) Prior Publication Data
US 2009/0088708 A1   Apr. 2, 2009

Related U.S. Application Data

(62) Division of application No. 10/762,884, filed on Jan. 22, 2004, now abandoned.

(60) Provisional application No. 60/442,603, filed on Jan. 25, 2003.

(51) Int. Cl.
*A61B 17/04* (2006.01)
(52) U.S. Cl. ..................................... 606/232
(58) Field of Classification Search .............. 606/60, 606/103, 139, 144, 148–150, 213, 215, 216, 606/246, 263; 623/13.13, 13.14, 19.11, 23.72; 128/898, 899
See application file for complete search history.

(56) References Cited

U.S. PATENT DOCUMENTS

| | | | |
|---|---|---|---|
| 3,650,274 A | | 3/1972 | Edwards et al. |
| 4,535,772 A | | 8/1985 | Sheehan |
| 5,127,412 A | * | 7/1992 | Cosmetto et al. ............ 128/898 |
| 5,571,138 A | | 11/1996 | Blomqvist et al. |
| 5,893,879 A | | 4/1999 | Hirshowitz et al. |
| 5,947,983 A | | 9/1999 | Solar et al. |
| 6,120,525 A | | 9/2000 | Westcott |
| 6,471,715 B1 | * | 10/2002 | Weiss ........................ 606/216 |
| 6,485,503 B2 | | 11/2002 | Jacobs et al. |
| 7,361,185 B2 | * | 4/2008 | O'Malley et al. ........... 606/215 |
| 2003/0229361 A1 | | 12/2003 | Jackson |

OTHER PUBLICATIONS

Proxiderm Procedure; © Copyright 2001 Progressive Surgical Products; www.proxiderm.com.

* cited by examiner

*Primary Examiner*—Melanie Tyson
(74) *Attorney, Agent, or Firm*—Caesar, Rivise, Bernstein, Cohen & Pokotilow, Ltd.

(57) ABSTRACT

A method for treating a wound with sutures is disclosed. One method includes placing the body and shaft of the device within a cavity of the wound; attaching a first end of at least one suture to a first side of the wound; passing a second end of the at least one suture through the body and coupling it to the shaft; attaching a second end of the at least one suture to the second side of the wound; and rotating the shaft with respect to the body to pull the first side of the wound and the second side of the wound toward one another.

5 Claims, 11 Drawing Sheets

METHOD FOR TREATING A WOUND

CROSS REFERENCE TO RELATED APPLICATIONS

This application claims priority to U.S. patent application Ser. No. 10/762,884 filed Jan. 22, 2004, now abandoned, which claimed priority to U.S. Provisional Application Ser. No. 60/442,603 filed on Jan. 25, 2003.

FIELD OF THE INVENTION

This invention relates to a method for treating and closing wounds. More particularly this invention relates to a method for treating and closing wounds from within the wound cavity.

BACKGROUND OF THE INVENTION

Historically there have been efforts to close difficult wounds by utilizing skin stretching devices that apply tension on the skin surrounding the wound. The application of tension to the skin causes the skin to stretch and ultimately the wound can be closed. While this technique has been effective for shallow wounds, it has not been successful for large wounds, especially those that form large cavities. Often, the skin surrounding the cavity wound is stretched such that it completely covers the cavity and is sutured closed. This can lead to the formation of a fluid filled pocket, seroma, beneath the stretched skin at the location of the wound. An infection can form in the seroma and ultimately the original cavity wound returns. These wounds may become chronic in nature and can persist for many months or even years. They are a tremendous burden on the patient and society. As such, there is a need for a device that applies tension to the tissue surrounding a wound, so that this tissue can be pulled in to fill the cavity. Additionally, some surgical wounds can be difficult to close and often there is a benefit to delayed surgical closure. A device that can aid in gradual closure over a period of time is beneficial.

A second conventional technique to heal wounds is the application of suction to the wound to drain the wound. Wound drainage has been known to be an important technique in the promotion of wound healing for many decades and is used for both open and closed wounds. For open wounds, drainage is accomplished by placing a drain tube in the wound, covering the wound and attaching suction to the drain tube. The application of suction is thought to promote wound healing by draining the wound of deleterious wound exudate and encouraging wound healing activity in the surrounding tissue. Existing wound tensioning devices extend outward and upward beyond the margins of the wound, making it impossible or impractical to seal the wound so that suction may be applied in combination with tension.

SUMMARY OF THE INVENTION

To overcome the deficiencies of conventional wound treatment techniques, the present invention is a method for use with sutures to repair a wound of a patient.

The device is for placement within an open wound and comprises an external member and an internal member rotatably coupled to the external member. The internal member has at least one receiver for receiving the at least one suture.

According to one aspect of the invention, at least one suture is passed through or otherwise coupled to the at least one receiver in the internal member. The at least one suture is coupled to portions of the wound and tightened by rotating the internal member in a first direction to draw portions of the wound toward one another.

According to another aspect of the invention, the at least one receiver is an aperture extending radially through the shaft, a hook disposed within the shaft, a substantially "T" shaped element coupled to an external portion of the shaft, and/or a substantially hook shaped element coupled to an external portion of the shaft.

According to a further aspect of the invention, the device comprises a body having at least one aperture extending radially through the body. A shaft is at least partially disposed within and rotatably coupled to the body, and the shaft has a plurality of apertures and/or slots substantially in line with the at least one aperture in the body. The plurality of apertures are spaced apart from one another and extend radially through said shaft.

According to one aspect of the invention, sutures are applied to the tissue near the perimeter of the wound and then passed through the device. Once all sutures have been secured, the device is used to pull the sutures and tissue inward toward the central portion of the wound. This tensioning and resulting movement is accomplished by winding the sutures around the shaft within the outer tubular portion of the device. The amount and direction of force applied to the tissue can be controlled by the caregiver.

Applying tension to the tissue near the perimeter of the wound serves to pull the tissue towards the central portion of the wound, which ultimately decreases the size of the wound and then allows for complete closure of the wound. As the wound size decreases, the caregiver can check the wound and adjust the device to maintain tension on the tissue.

According to a further aspect of the present invention, the device can also incorporate a port for attachment to a drain tube. The device can be placed in the wound, a drain tube attached to the device, and the wound and device can be covered with a sealing film. The drain tube can then be attached to a source of suction so that the wound may benefit from all of the positive aspects of wound drainage.

The invention also provides methods for treating a wound. One such method comprises the steps of placing at least one suture between points on a margin of the wound, applying tension to the at least one suture from within the wound, and maintaining the tension on the at least one suture for a predetermined period of time.

According to another aspect of the invention, a method for treating a wound comprises the steps of placing the at least one suture between points on a margin of the wound; applying tension to the at least one suture; maintaining the tension on the at least one suture for a predetermined period of time; and applying a vacuum to the wound.

According to another aspect of the invention, a method for treating a wound comprises the steps of providing a tubular body having at least one aperture and/or slot extending radially through the tubular body; rotatably coupling a shaft within the tubular body, the shaft having a plurality of receivers capable of being substantially aligned with the at least one aperture and/or slot in the tubular body; placing the tubular body and the shaft within a cavity of the wound; attaching a first end of at least one suture to a first side of the wound; passing a second end of the at least one suture through the tubular body and the shaft; attaching the second end of the at least one suture to second side of the wound; and rotating the shaft with respect to the tubular body to pull the first side of the wound and the second side of the wound toward one another.

According to another aspect of the present invention, the wound is sealed with the device within the wound cavity, and suction is applied to the device for draining the wound.

BRIEF DESCRIPTION OF THE DRAWINGS

The invention is best understood from the following detailed description when read in connection with the accompanying drawing. It is emphasized that, according to common practice, the various features of the drawing are not to scale. On the contrary, the dimensions of the various features are arbitrarily expanded or reduced for clarity. Included in the drawing are the following Figures.

DETAILED DESCRIPTION OF THE INVENTION

Figure 1:
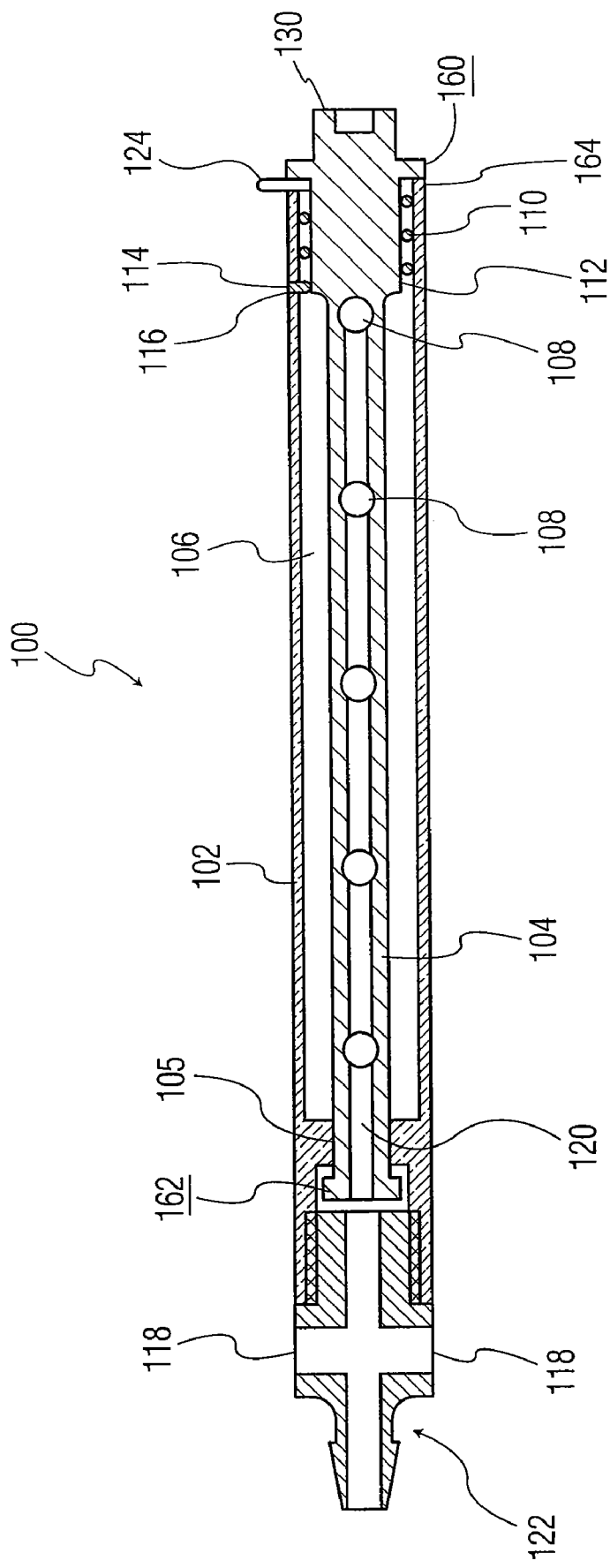
FIG. 1 is a cross sectional view of an exemplary embodiment of the present invention.

Referring to FIG. 1, a cut-away side view of a first exemplary embodiment of the present invention is illustrated. As shown in FIG. 1, device 100 comprises external tube 102 having a hollow portion 106, and internal shaft 104 rotatably coupled to tube 102 at bearing portion 105. Internal shaft 104 has a plurality of receivers 108, such as holes or slots that pass through the radius of internal shaft 104 (best shown in FIG. 5A). As used herein, receiver is intended to refer to a feature of shaft 104 for interfacing and or attaching with sutures described below. Although hollow portion 106 is illustrated between an outer surface of shaft 104 and an inner wall of tube 102, it is possible to construct device 100 such that shaft 104 and tube 102 are in a close spaced relationship such that there is a minimum clearance allowing for rotation of shaft 104 without binding against tube 102.

Internal shaft 104 is desirably maintained within external tube 102 by the cooperation of bearing portion 105 with first end portion 162 of internal shaft 104, and the cooperation of second end portion 160 of internal shaft 104 within end 164 of external tube 102.

Referring now to FIGS. 3A, 4 and 5A-5C, in use, device 100 is placed within the interior of wound 140. Sutures 132 are passed through holes 109 in external tube 102 (best shown in FIGS. 3 and 5A) and through holes 108 in internal shaft 104. Sutures 132 are desirably attached to opposing portions 134, 136 of wound 140.

Figure 5A:
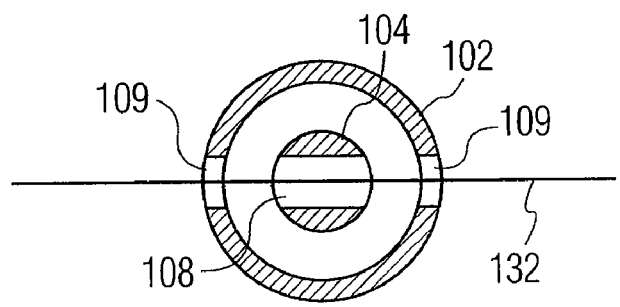
FIGS. 5A, 5B and 5C are end views of the device of FIG. 1 illustrating tensioning of the sutures.
Figure 5B:
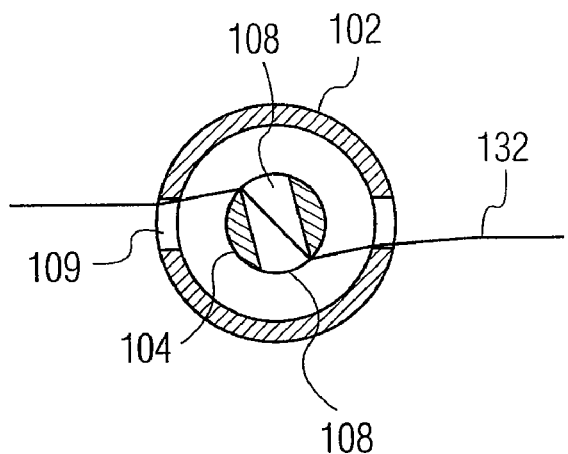
Figure 5C:
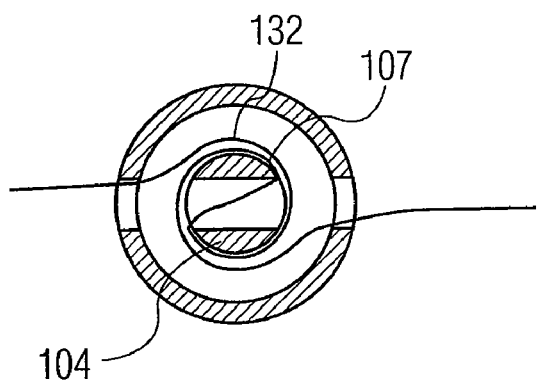
Figure 6A:
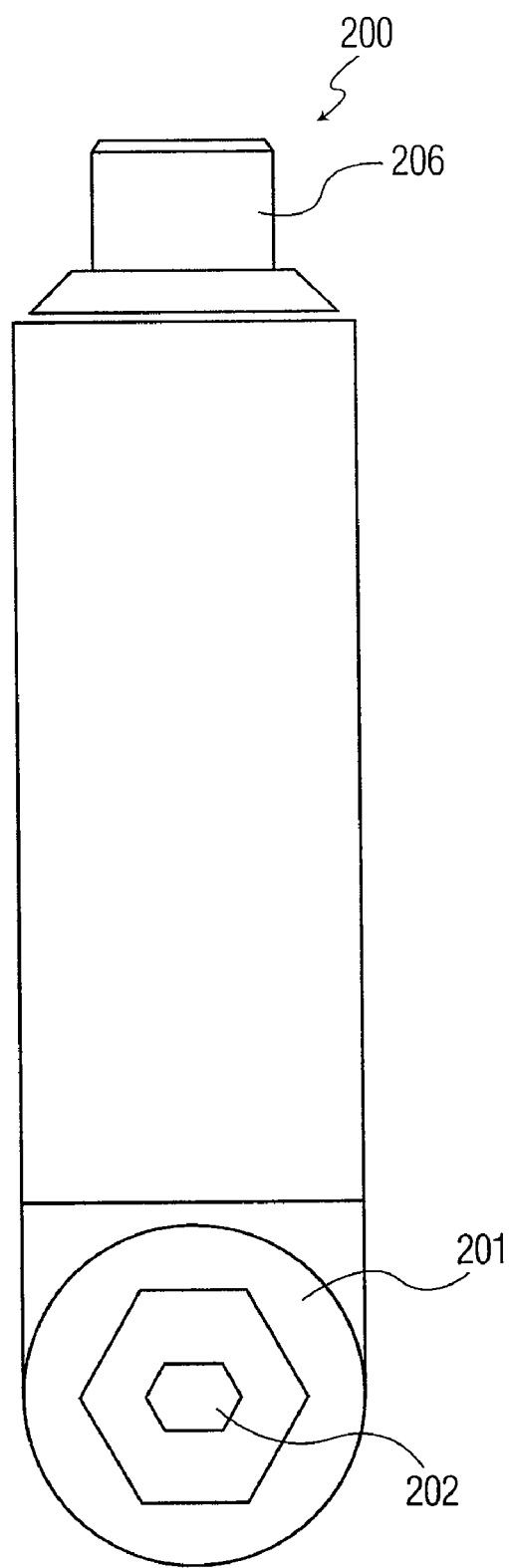
FIGS. 6A-6B illustrate an exemplary apparatus that can be used to tighten the exemplary embodiment of FIG. 1.
Figure 6B:
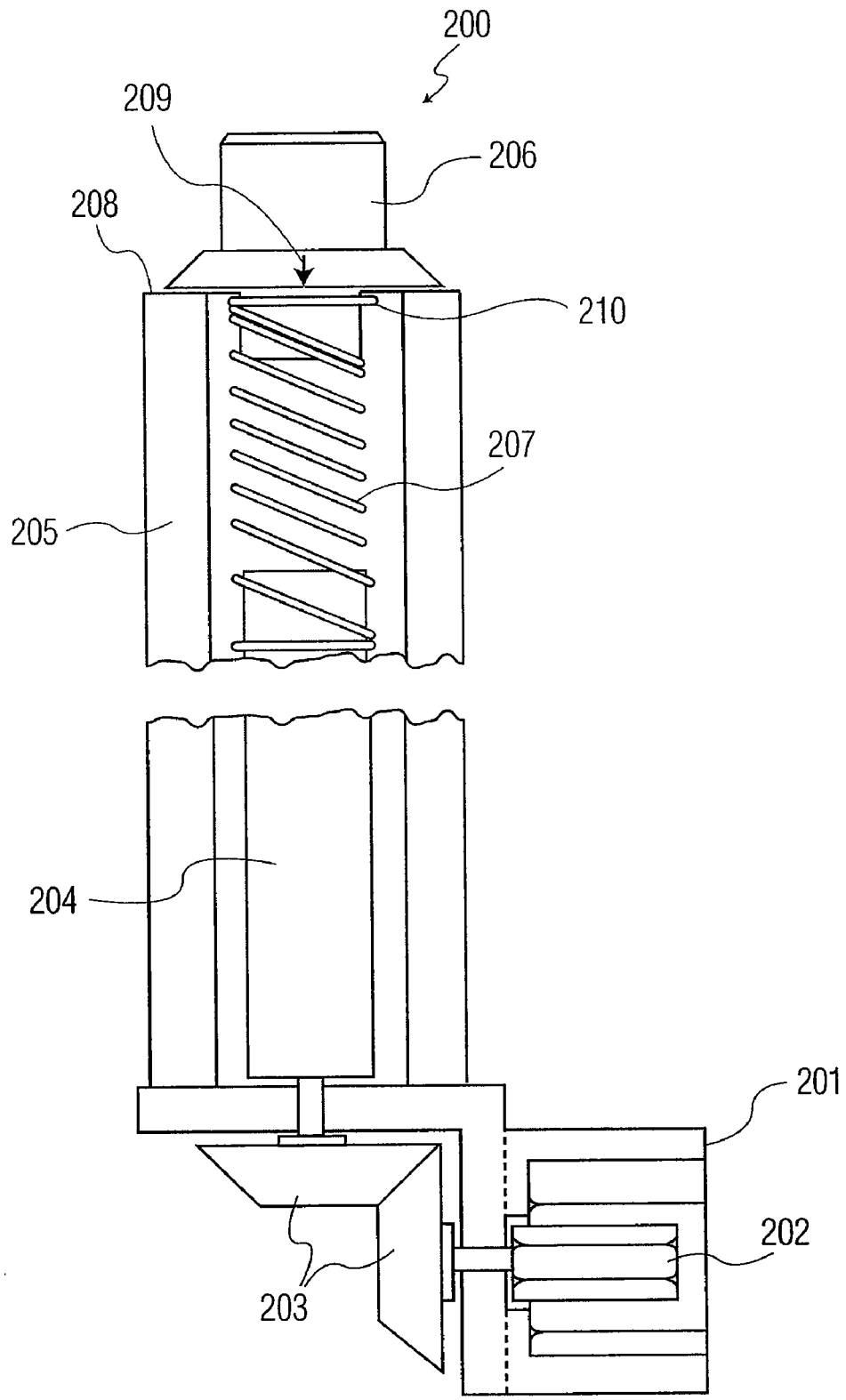

Driving mechanism 200 (best shown in FIGS. 6A-6B) can be detachably connected to end 130, such as a slotted or hex head for example, and used to rotate internal shaft 104 within external tube 102. As illustrated in FIGS. 5A-5C, internal shaft 104 is rotated and sutures 132 are wrapped around an exterior portion 107 of shaft 104. This, in turn, pulls sutures 132 and the attached tissue of wound 140 towards device 100, which is desirably located in the central portion of wound 140, thereby creating tension on the subcutaneous tissue and pulling the tissue toward the center of the wound, thus promoting healing of the wound.

Figure 2:
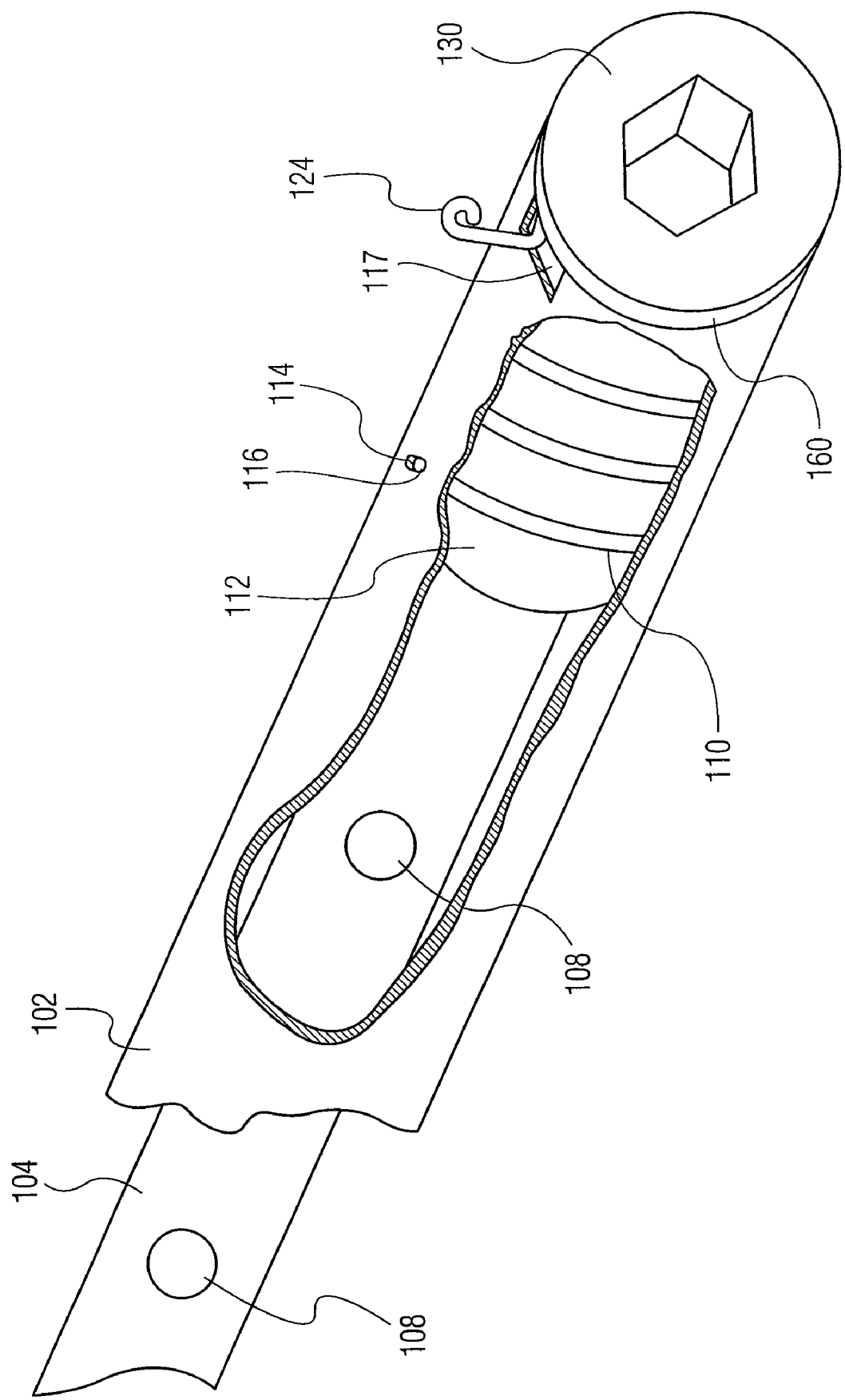
FIG. 2 is a cut away view of a portion of the exemplary embodiment of FIG. 1.

Referring now to FIGS. 1 and 2, in one exemplary embodiment of the present invention, coil spring 110 may be disposed around a portion of internal shaft 104 with a first end of coil spring 110 coupled to a first portion of tube 102. In one desirable implementation, coil spring 110 fits snuggly around shaft 104 at end 112. A first end 114 of coil spring 110 is coupled to external tube 102, by passing through hole 116 of tube 102 for example. A second end 124 of coil spring 110 may pass through an opening 117, such as slot, in tube 102 or may extend beyond the end of tube 102, for example. In this configuration, coil spring 110 acts as a clutch permitting shaft 104 to easily rotate in only one direction during normal use. In operation, coil spring 110 is wound in a counterclockwise direction about shaft 104 as coil spring 110 progresses from an inner portion of internal shaft 104 toward an end of internal shaft 104. As shaft 104 is rotated in a direction opposite to the direction of the coil spring, that is in clockwise direction, coil spring 110 is forced to open, thus increasing the diameter of coil spring 110. This increase in diameter allows the shaft to rotate freely. When the shaft rotates slightly in the direction of the spring, counter clockwise, the spring diameter decreases preventing shaft 104 from unintentional unwinding, thus ensuring that tension remains on sutures 132 and the tissue.

If it is necessary to loosen the sutures by unwinding the shaft 104, the pressure exerted by coil spring 110 may be relieved by moving end 124 of coil spring 110 in a clockwise direction. This in turn relieves the pressure exerted by coil spring 110. Shaft 104 will then be able to rotate in the counterclockwise direction as desired.

Figure 3A:
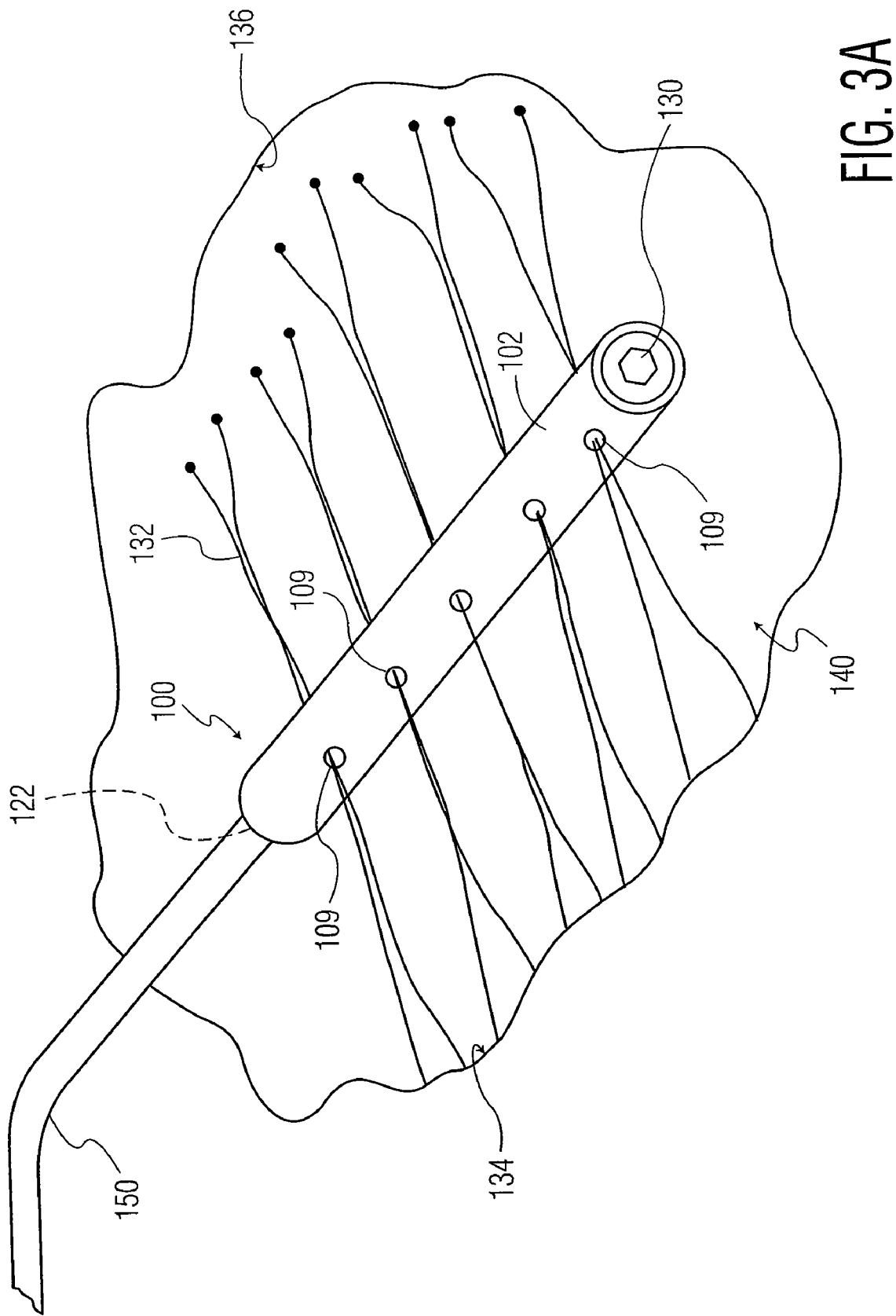
FIG. 3A is a perspective view of the exemplary embodiment of FIG. 1 installed in a cavity wound, illustrating sutures attached to the subcutaneous tissue at the perimeter of the wound.

Referring now to FIGS. 3A and 4-5C, use of device 100 is illustrated. As shown in FIG. 3A, device 100 is desirably placed in the central portion of the wound 140. Sutures 132 are secured to tissue 134 on one side of wound 140 and then passed through the holes 108, 109 of tube 102 and shaft 104, respectively. Sutures 132 are then secured to the tissue 136 on the opposite sides of wound 140. Once sutures 132 have been secured, device 100 is used to pull sutures 132 and connected tissue towards the center of wound 140.

In one exemplary embodiment of the present invention, the amount of tension applied to the tissue by sutures 132 can be controlled by using a torque wrench. A ratcheting torque wrench or screwdriver, for example, may be used to wind sutures 132 around shaft 104. A torque wrench is desirable because it can indicate the amount of torque applied to shaft 104. The torque applied to shaft 104 is proportional to the tension on sutures 132 and the attached tissue. Each time shaft 104 is turned, the caregiver will apply a predetermined force to the sutures. For example, one (1) pound of force per suture is adequate to effect closure of the wound. Alternately the clinician may choose to tighten the wound based on feel. As healing of wound 140 progresses, the tissue moves toward the device in the central portion of wound 140; thus, the tension may decrease. In view of this decrease in tension, device 100 will then need to be tightened again.

In addition to applying tension to the tissue near the perimeter of wound 140, it may also be necessary to drain wound 140 with suction. Referring again to FIGS. 1 and 3A, in one exemplary embodiment, drainage tube 150 may be attached to vacuum port 122 of device 100. In the illustrated configuration, vacuum port 122 is coupled to an end portion of tube 102. In one configuration, vacuum port 122 may be coupled to and in a fluid tight relationship with ports 118 that exit tube 102. In a second configuration, shaft 104 may include a longitudinal orifice 120 that extends from one end of tube 104 adjacent vacuum port 122. Orifice 120 is coupled to vacuum port 122 and radial holes 108 in a fluid tight relationship so that vacuum provide at port 122 is imparted into wound 140 through holes 108. It is also contemplated that ports 118 may be combined with this latter configuration to provide vacuum in a greater area of the wound, if desired.

Vacuum port 122 is optional and is not needed to treat wounds that do not require suction drainage. In the event that suction drainage is required, the wound is preferably covered with an airtight dressing (not shown) to ensure that suction is maintained and to prevent drying and bacteria incursion. Drainage tube 150 desirably extends beyond such a wound cover. Drainage tube 150 may then be attached to a standard hospital wall suction canister or to a standard manually actuated wound drainage device (not shown), such as a squeeze bulb for example. Generally the wound may also be filled with a wound packing material (not shown) such as gauze or other suitable packing material. In cases where suction drainage is used, the wound exudate that has accumulated in the wound packing and surrounding wound is sucked into the device and then into drainage tube 150. Wound exudate may enter the device through a number of openings. In the exemplary embodiment of FIG. 1, the exudate may enter through ports 118. Additionally, exudate may enter outer tube 102 through holes 109, enter shaft 104 through holes 108, pass through longitudinal orifice 120 and then ultimately out through vacuum port 122 and into drainage tube 150.

Alternatively, it is possible to dispose drainage tube 150 adjacent device 100 within the cavity of wound 140. In such a case, the aforementioned ports and coupling in device 100 are not necessary.

Figure 3B:
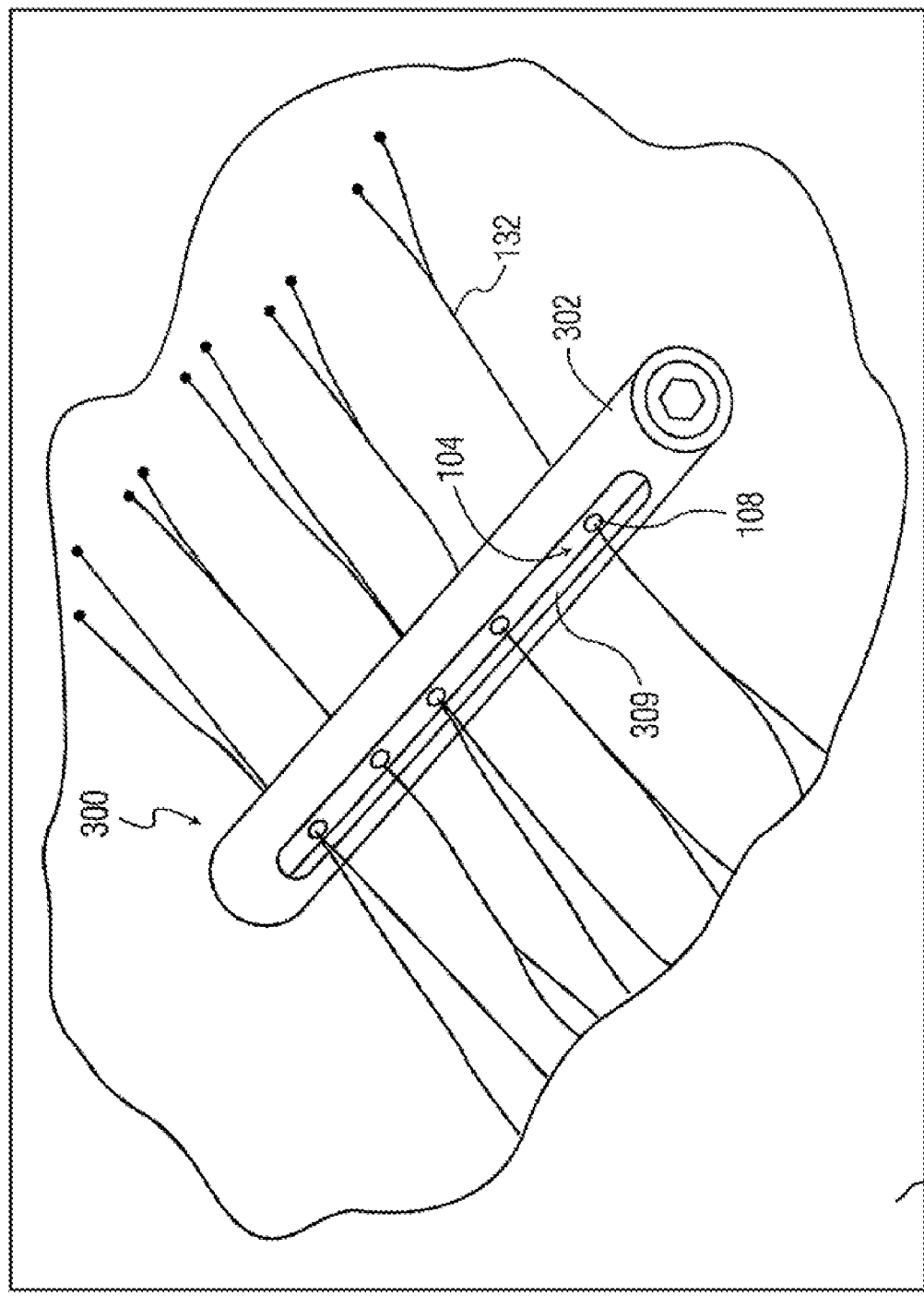
FIG. 3B is a perspective view of another exemplary embodiment of FIG. 1 installed in the cavity wound.
Figure 4:
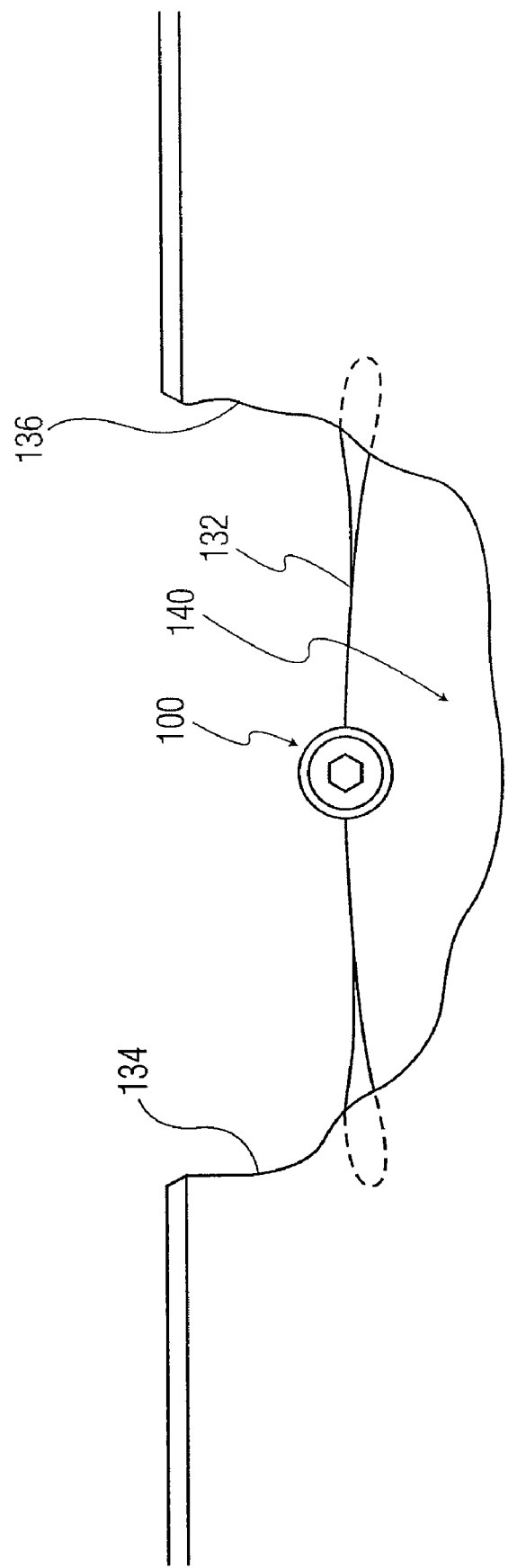
FIG. 4 is a side-view of the wound with the exemplary embodiment of FIG. 1 in place.

Referring now to FIG. 3B, an alternate embodiment of the device illustrated in FIG. 1 is shown. As shown in FIG. 3B, device 300 comprises a body 302 having an elongate passage 309 that is in alignment with receivers 108. As mentioned above, receivers 108 may be holes that extend radially through internal shaft 104, or may be another feature by which sutures 132 are held in proximity to shaft 104 so that sutures 132 are tensioned as shaft 104 is rotated with respect to body 302. FIG. 3B shows cover 350 over the wound and device 300.

Figure 7:
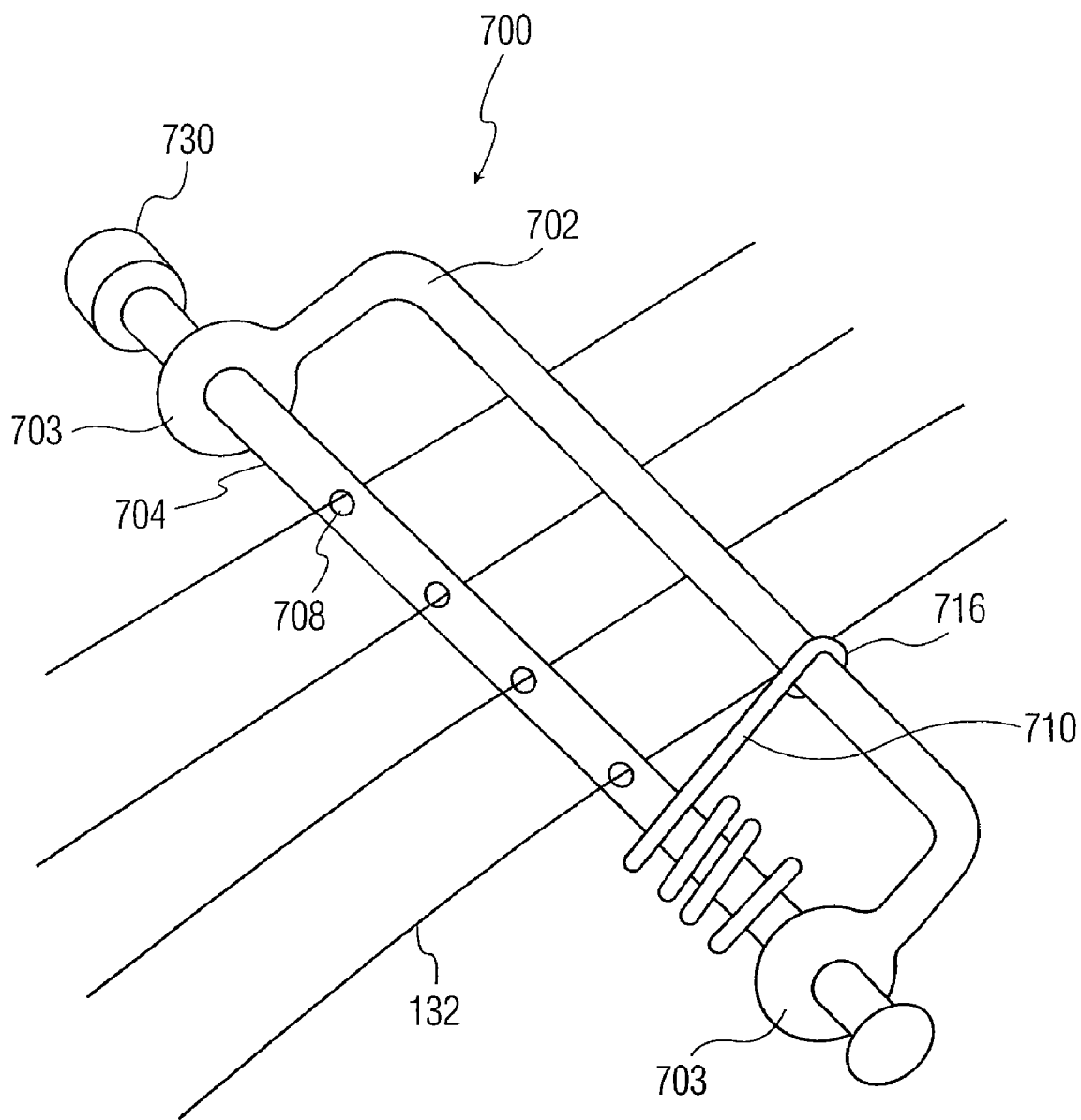
FIG. 7 illustrates another exemplary embodiment of the present invention.

FIG. 7 illustrates another exemplary embodiment of the present invention. As shown in FIG. 7, device 700 comprises shaft 704 and body 702. Body 702 is formed substantially in a "U" shape with couplings 703 disposed at opposite ends. Shaft 704, having receivers 708 for receiving and/or capturing sutures 132 disposed along at least a portion of the length of shaft 704, is rotatably coupled to body 702 at couplings 703. Similar to the exemplary embodiments described above, coil spring 710 may be optionally disposed around the circumference of shaft 704 at one end to allow rotation in a desired direction and prevent unintentional reversal of shaft 704 in operation. To maintain coil spring 710 in place, one end 716 is desirably coupled to a portion of body 702. In all other respects this exemplary embodiment is similar to the aforementioned embodiments and may include various other features of those embodiments.

Figure 8A:
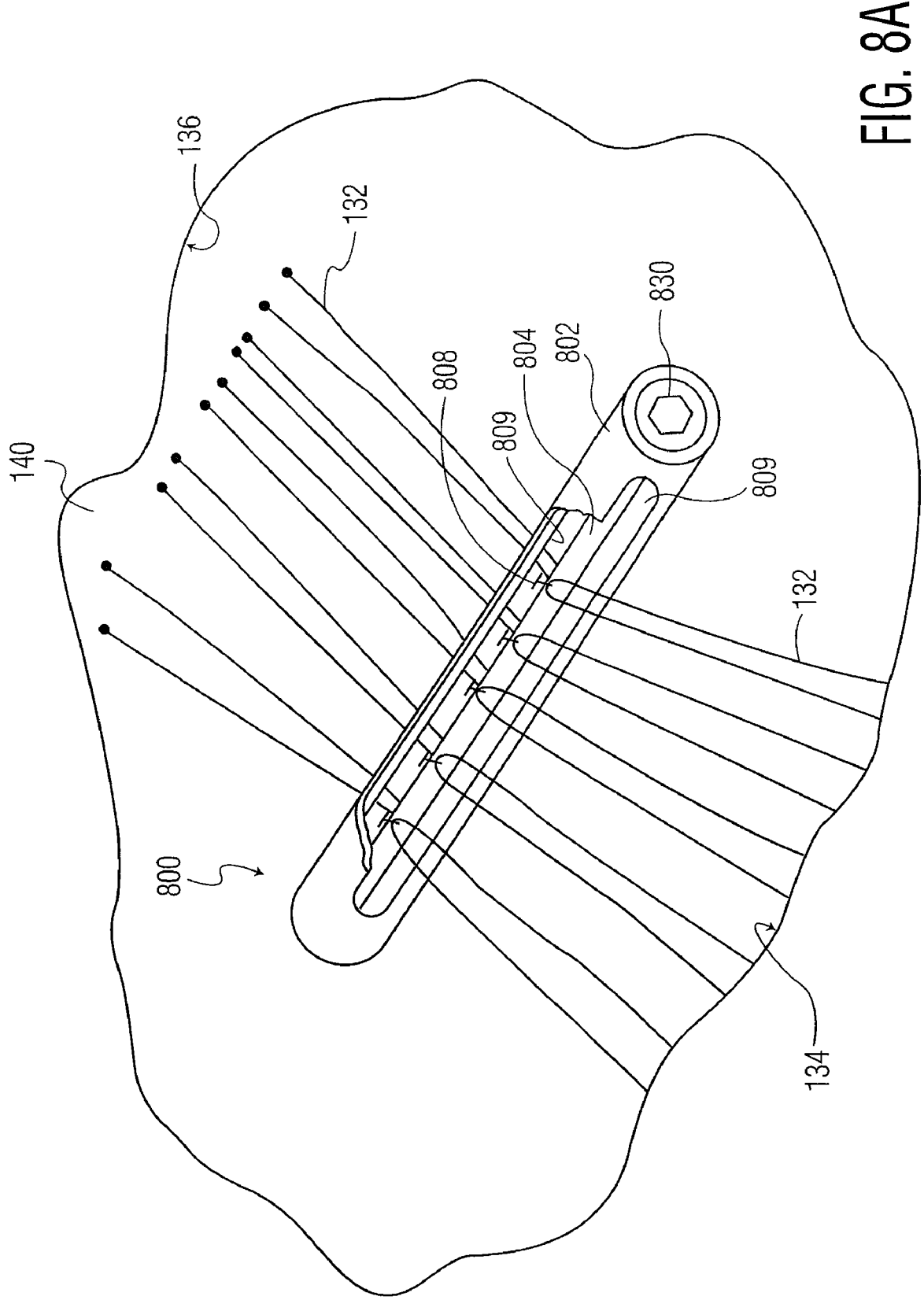
FIGS. 8A-8B illustrate a further exemplary embodiment of the present invention.
Figure 8B:
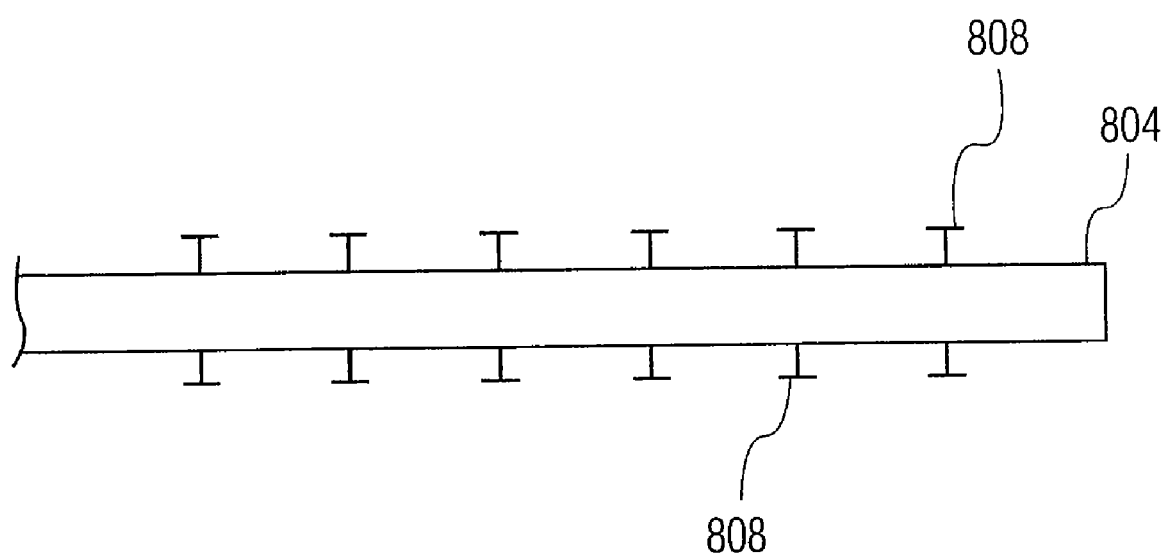

FIGS. 8A-8B illustrate yet another exemplary embodiment of the present invention. As shown in FIG. 8A, device 800 comprises body portion 802 and a shaft portion 804 rotatably coupled to body portion 802. Body portion 802 has at least one aperture 809 extending radially through body portion 802 such that sutures 132 may be passed into the central portion of body 802 to gain access to shaft 804. One difference between this embodiment and the embodiments of FIG. 1 is the use of receivers 808 disposed on the surface of shaft 804. Receivers 808 may have a "T" shape for example (best shown in FIG. 8B) and spaced apart from one another along a portion of the length of shaft 804. Although a "T" shape is illustrated the invention is not so limited in that other types of receivers may be used, such a those having a hooked or "U" shape for example, or any other type of receiver capable of attaching to and/or grabbing a portion of suture 132 such that suture 132 may be tensioned as shaft 804 is rotated with respect to body 802. In all other respects this embodiment is similar to the aforementioned embodiments.

An exemplary embodiment of a torque driver 200 such as that discussed above is illustrated in FIGS. 6A-6B. The exemplary driver is intended for the application of a specified torque desirably at right angles to the suture tensioner previously described. Other embodiments can be readily visualized in accordance with the following description.

Torque driver 200 is releasably attached to coupling 130 of device 100 by head end 201, such as a hex head. Drive portion 202 desirably engages coupling 130 of device 100. In the illustrated embodiment, drive portion 202 is driven at right angles by bevel gears 203 that are in turn driven by shaft 204 which is disposed within handle 205. Alternately, bevel gears 203 may be replaced with a flexible shaft (not shown). Shaft 204 is coupled to knob 206, such as a calibrated knob, via a spring 207. Indicator 209 on knob 206, such as an arrow, desirably points to calibrated scale 208 on a face of driver 200. Spring 207 is desirably calibrated to provide a predetermined amount of torque to gears 203 and ultimately to device 100 that is attached to the soft tissue in a patient.

Spring 207 can be wound such that the attachment point 210 of spring 207 to knob 206 carries a calibrated release characteristic such that a maximum torque will not be exceeded so as to protect the soft tissue of the patient.

The handle-knob arrangement can be so configured as to desirably permit one-handed operation. So that the entire assembly can be steadied in the wound cavity and the knob turned between the index and forefinger, for example.

The invention also includes methods for treating a wound. A first exemplary method comprises the steps of placing a tensioning device within a wound cavity, securing the tensioning device to the tissue near the perimeter of a wound and then applying tension to the tissue to draw the tissue towards the interior of the wound. A second exemplary method comprises the steps of applying a tissue tensioning device to a wound, the device being placed in the wound cavity, sealing the wound with the device within the wound cavity and attaching suction to the wound for wound drainage.

It is obvious to one skilled in the art that there are alternate embodiments of the invention that are useful. For example, while the preferred device is a linear device, a radial configuration in which sutures extend outward from a central point is useful, especially for wounds that are generally round. In another exemplary embodiment, the device may be sutured to the bottom of the wound. In this alternate embodiment, tightening of the device will put tension on the tissue on the bottom of the wound pulling generally upward, as well as tension on the tissue at the perimeter of the wound. In yet another embodiment of the present invention, a built in torque indicator may be incorporated.

Other features may be included in the invention. For example, the holes that pass through the internal shaft and tube may be replaced with slots. The inclusion of slots will give the doctor a broader range of options for the placement of sutures. A clamping element may also be included to lock the sutures to the central shaft and eliminate the need for knotting of the sutures. It may also be desirable to have sutures extend in the x, y and z directions.

Although the invention is illustrated and described herein with reference to specific embodiments, the invention is not intended to be limited to the details shown. Rather, various modifications may be made in the details within the scope and range of equivalents of the claims and without departing from the invention.

What is claimed:

1. A method to facilitate healing of a wound, the method comprising:
   providing an apparatus for applying a force to margins of said wound, said apparatus comprising a body having at least one aperture extending radially through said body;
   rotatably coupling a shaft to said body, said shaft having at least one aperture and/or slot capable of being aligned with said at least one aperture in said body;
   placing said body and said shaft within a cavity of said wound;
   attaching a first end of at least one suture to a first side of said wound;
   passing a second end of said at least one suture through said body and said shaft;
   attaching said second end of said at least one suture to a second side of said wound;
   covering the wound and the apparatus with a wound cover;
   applying the force to the margins of the wound with said apparatus by rotating said shaft with respect to said body to pull said first side of said wound and said second side of said wound toward one another; and
   applying suction to said wound to extract exudates from said wound and facilitate healing of the wound.

2. The method according to claim 1, wherein said wound is an open wound.

3. The method according to claim 1, further comprising further rotating said shaft to apply a predetermined tension between sides of said wound.

4. The method according to claim 3, further comprising detachably coupling a driver to said shaft to apply said predetermined tension.

5. The method according to claim 1, wherein the body has a plurality of apertures extending radially through said body, and said shaft has a respective plurality of apertures and/or slots capable of being aligned with said apertures in said body.

* * * * *